(12) United States Patent
Park

(10) Patent No.: US 7,731,688 B2
(45) Date of Patent: Jun. 8, 2010

(54) WARMING APPARATUS WITH HEATER PRODUCED BY PCB

(76) Inventor: Jae-Sang Park, #107-2009 Hyundae Apt., 1344, Bangbac dong, Sencho-gu, Seoul, 137-937 (KR)

(*) Notice: Subject to any disclaimer, the term of this patent is extended or adjusted under 35 U.S.C. 154(b) by 910 days.

(21) Appl. No.: 10/572,118

(22) PCT Filed: Sep. 17, 2004

(86) PCT No.: PCT/KR2004/002386
§ 371 (c)(1),
(2), (4) Date: Mar. 16, 2006

(87) PCT Pub. No.: WO2005/027578
PCT Pub. Date: Mar. 24, 2005

(65) Prior Publication Data
US 2007/0049869 A1 Mar. 1, 2007

(51) Int. Cl.
*A61F 7/12* (2006.01)
(52) U.S. Cl. .................................... 604/113
(58) Field of Classification Search ............. 422/46; 604/113, 4.01
See application file for complete search history.

(56) References Cited
U.S. PATENT DOCUMENTS
6,236,809 B1 * 5/2001 Cassidy et al. .............. 392/470
* cited by examiner

*Primary Examiner*—Kevin C Sirmons
*Assistant Examiner*—Deanna K Hall
(74) *Attorney, Agent, or Firm*—Fulbright & Jaworski LLP

(57) ABSTRACT

The disclosed invention relates to a heating apparatus having a PCB-type heater capable of allowing the temperature of Ringer's solution or blood which is introduced into a blood vessel, when transfusing a blood thereto, to be equal to that of the human body to thereby provide an accurate resistance value. The present invention comprises 1. A heating apparatus according to an embodiment of the invention comprises a body including a first connecting portion having a tube which is connected to the first connection portion and receives a fluid supplied from an instillation room, a path having the shape of a spiral screw thread to enable the fluid to flow and a second connecting portion for supplying the fluid flowing through the path to an injection syringe; an inner cover inserted into the body and fixedly attached thereto in a prescribed adhesive manner for preventing the fluid from flowing out; a middle cover for closely fixing the body and the inner cover against each other; a PCB-type heater inserted into the inside of the top and bottom surfaces of the middle cover for heating the fluid flowing through the path so that the fluid is maintained at a prescribed temperature; a bottom case having a box portion to receive the body having the heater and the middle cover coupled thereto; and a upper case coupled to the bottom case.

20 Claims, 15 Drawing Sheets

US 7,731,688 B2

WARMING APPARATUS WITH HEATER PRODUCED BY PCB

RELATED APPLICATIONS

This application is a 371 of PCT/KR04/02386 Sep. 17, 2004.

TECHNICAL FIELD

The present invention relates to a heating apparatus comprising a printed circuit board type ("PCB-type") heater and more particularly, to a heating apparatus having a PCB-type heater capable of allowing the temperature of Ringer's solution or blood which is introduced into a blood vessel, when transfusing a blood thereto, to be equal to that of the human body using the PCB-type so as to provide an accurate resistance value.

BACKGROUND ART

Typically, a method of dosing a patient with a chemical material which is useful to him/her includes taking medicine and injecting it. A method of injecting medicine into the patient includes a hypodermic injection, an intra-muscular injection, intravenous injection and so on. Among them, the intravenous injection is applied when injecting into a blood vessel for a long time. For example, the intravenous injection is used when supporting a blood or giving an injection of Ringer's solution to a patient and generally uses an intravenous drip set.

The Ringers solution is usually kept at a low temperature in order to prevent from being decomposed or producing an alien substance, and a blood and the like are usually kept in cold environment in order to prevent any noxious eutrophication of an organic matter prior to giving a blood transfusion to patient. Generally, the temperature of Ringer's solution and blood is in a circumstance of 20° C. or less when injecting to a human body. Accordingly, when Ringer's solution or blood is injected to a human body, the temperature thereof also rises since the temperature of human body is generally 37°. In this case, the energy that the temperature of Ringer's solution or blood is required to rise to human body is supplied by the patient's risen metabolic rate. Since this thermal load is never feeble compared to the normal metabolic rate, it drops human body's temperature and excites a cooling point of skin. As a result, under such a situation, any injection of Ringer's solution or giving of a blood transfusion to patient may cause a cold pain to the patient and even make the lives of the patient very dangerous.

In order to solve such problems, a Korean Patent No. 130926 discloses a method and apparatus for medicine for allowing the temperature of Ringer's solution or blood to be equal to that of human body prior to injecting Ringer's solution or blood to the patient.

According to the above Patent No. 130926, a tube is fixed to the upper portion of a panel in order to adjust the temperature of Ringer's solution and a first cover is placed on the upper portion of the panel. The first cover is fixed to a vertical member by means of a hinge, and a locking device is installed on a horizontal member opposed to the vertical member having the hinge attached thereto. The first cover is attached with a second cover having a built-in insulation on the upper portion thereof. Therefore, the tube is built-in within a rectangular-shape barrel as a whole and is heated by a heating means within a rectangular barrel.

Since the tube within the rectangular-shape barrel is short in the length thereof, a heating apparatus for medicine which should heat at a low temperature of 41.5° or less is substantially difficult to rise the short tube in length to a desired temperature and control a desired temperature. Further, when using a high-temperature heating apparatus which would cause harmful effects, a very fine electronic control system for controlling the high-temperature heating apparatus should be applied, resulting in the complexity of the heating apparatus and a high cost of production thereof.

Also, a heating apparatus using a conventional Ni—Cr heating resistor is designed to wind a surface of a circular-shaped heating resistor with a tube such as Ringer's solution, cover the surface with a lid and then lock by means of a locking device. However, this structure has a troublesome and complexity since the heating resistor should be wound with the tube whenever using it. Further, the use of Ni—Cr heating resistor causes the size of the heating apparatus to be large and the weight reaches more than 20 Kg, resulting in a very heavy expense of the heating apparatus.

DISCLOSURE OF THE INVENTION

Accordingly, the present invention has been made in view of the above problems, and it is an object of the present invention to provide a heating apparatus having a PCB-type heater capable of allowing the temperature of Ringer's solution or blood which is introduced into a blood vessel, when transfusing a blood thereto, to be equal to that of the human body using the PCB-type heater designed to provide an accurate resistance value as a heating means.

Other object of the present invention is to provide a heating apparatus having a PCB-type heater in which a heating resistor is formed on a printed circuit board using two different materials having a large thermoelectric power, a thermocouple is formed by the two materials, a heating temperature of the heating resistor is measured and controlled.

Another object of the present invention is to provide a heating apparatus having a PCB-type heater which can be conveniently by supplying a DC Power to the heater using a DC power supply.

To achieve the above object, according to an embodiment of the present invention, there is provided a heating apparatus comprising: a body including a first connecting portion having a tube which is connected to the first connection portion and receives a fluid supplied from an instillation room, a path having the shape of a spiral screw thread to enable the fluid to flow and a second connecting portion for supplying the fluid flowing through the path to an injection syringe; an inner cover inserted into the body and fixedly attached thereto in a prescribed adhesive manner for preventing the fluid from flowing out; a middle cover for closely fixing the body and the inner cover against each other; a PCB-type heater inserted into the inside of the top and bottom surfaces of the middle cover for heating the fluid flowing through the path so that the fluid is maintained at a prescribed temperature; a bottom case having a box portion to receive the body having the heater and the middle cover coupled thereto; and a upper case coupled to the bottom case.

According to another embodiment of the present invention, there is provided a heating apparatus comprising: a body including a first connecting portion having a tube which is connected to the first connection portion and receives a fluid supplied from an instillation room, a path having the shape of a zigzag to enable the fluid to flow, and a second connecting portion for supplying the fluid flowing through the path to an injection syringe; an inner cover fixedly attached, in a prescribed adhesive manner, to the surface on which the path is formed for preventing the fluid from flowing out; a middle cover for closely fixing the body and the inner cover against each other; a PCB-type heater inserted into at least one inside of the inside of the body and the inside of the middle cover for heating the fluid flowing through the path so that the fluid is maintained at a prescribed temperature; a bottom case having a box portion to receive the body having the heater and the middle cover coupled thereto; and a upper case coupled to the bottom case.

Further, the upper case comprises; a power supply button for supplying or breaking a power to the heater in accordance with a user's operation; an operation display for displaying whether or not the heater is normally operating; an alarm device for alarming when the heater is operating in error; a temperature indicator for indicating the heating temperature of the heater; and a temperature setting button for adjusting the heating temperature of the heater in accordance with a user's operation.

Meanwhile, the PCB-type heater is inserted into the inside of the body.

The PCB-type heater the heater is formed of: an insulating substrate; a heating resistor being formed on the upper portion of the insulating substrate by a circuit pattern designed to have a uniform resistance value and generating a heat corresponding to a heat capacity which was re-designed in accordance with the power being supplied; a power supply terminal for supplying a power to the heating resistor; a coupling terminal being coupled to a temperature sensor which measures the temperature of the fluid flowing through the body; a sensor connecting terminal being connected to the coupling terminal for reading the measured temperature from the outside; and an insulating protection film for protecting the heating resistor, wherein the heater further comprising a control circuit formed on a prescribed area or the bottom portion of the insulating substrate for controlling the degree of heating of the heater.

BRIEF DESCRIPTION OF THE DRAWINGS

The above and other objects and features of the invention will become apparent from the following description of preferred embodiments taken in conjunction with the accompanying drawings, in which.

BEST MODES FOR CARRYING OUT THE INVENTION

The present invention will now be described in detail in connection with preferred embodiments with reference to the accompanying drawings.

Example 1

Figure 1:
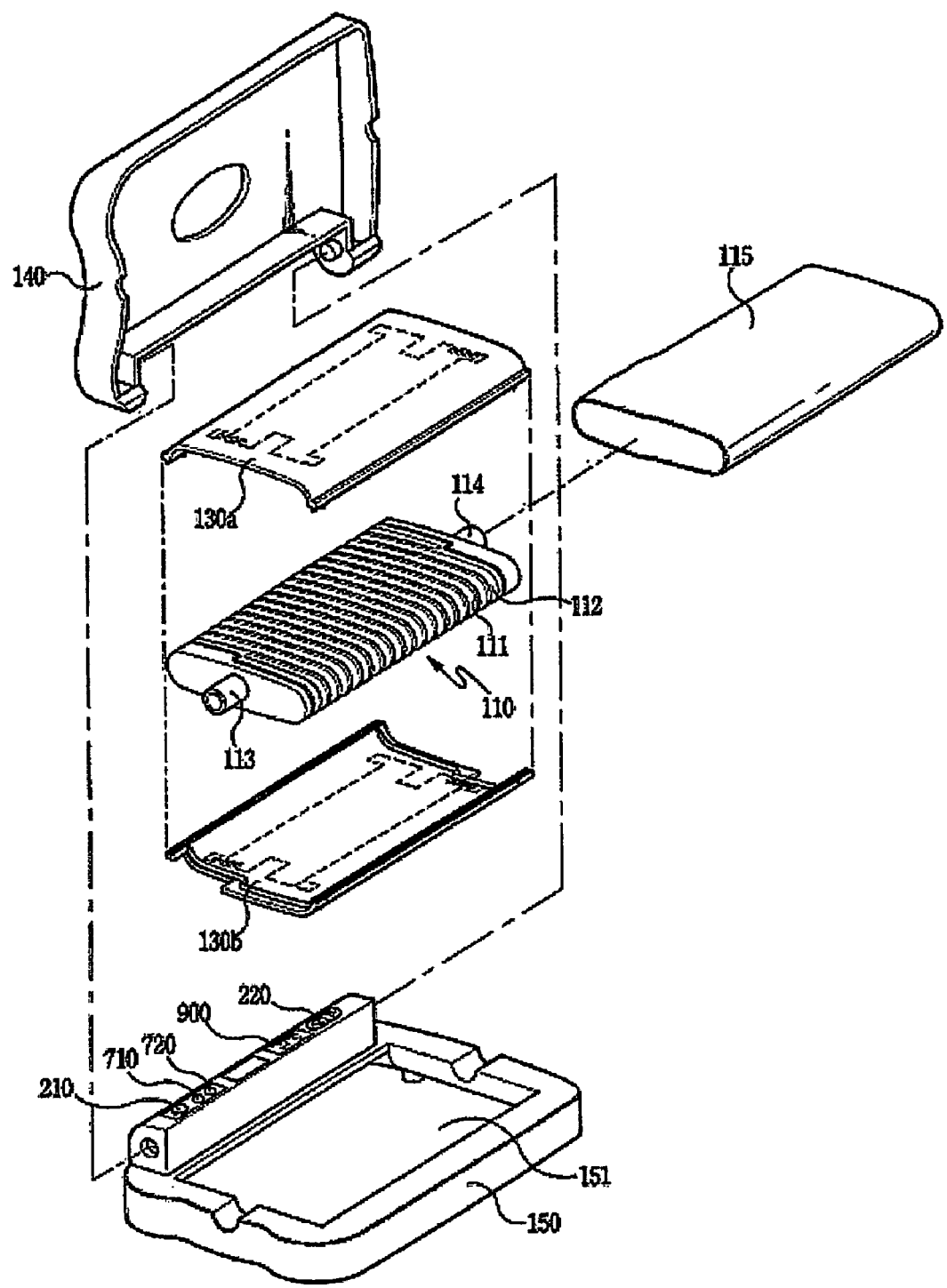
FIG. 1 is a separate prospective view illustrating a heating apparatus having a heater manufactured in accordance with the present invention.

FIG. 1 shows a separate prospective view illustrating a heating apparatus having a PCB-type heater in accordance with the present invention. As shown in FIG. 1, the heating apparatus comprises a body 110 including a first connecting portion 113 having a tube which is connected to the first connection portion 113 and receives a fluid supplied from an instillation room, a path 112 having the shape of a spiral screw thread to allow the fluid to flow and a second connecting portion 114 for supplying the fluid flowing through the path 112 to an injection syringe; an inner cover 115 inserted into the body 110 and fixedly attached thereto in a ultrasonic, high-frequency, or adhesive manner for preventing the fluid from flowing out; middle covers 130a, 130b for closely fixing the body 110 and the inner cover 115 against each other; a PCB-type heater 100 inserted into the inside of the top surface 130a and bottom surface 130b of the middle cover for heating the fluid flowing through the path 112 so that the fluid is maintained at a prescribed temperature; a bottom case 150 having a box portion 151 to receive the body 110 having the heater 100 and the middle cover 130a, 130b coupled thereto; and a upper case 140 coupled to the bottom case 150.

The body 110 and the middle covers 130a, 130b are made of different materials. For example, the material of the body 110 is ABC and the material of the middle covers 130a, 130b is PE. The body 110 and the middle covers 130a, 130b are combined each other in a ultrasonic adhesive manner.

As other adhesive manner, the middle covers 130a, 130b can be adhesively coupled to the body 110 by pressing a PE tube having a good contraction against the body 110 and combining the middle covers 130a, 130b.

Herein, one top side of the upper case 140 comprises a power supply button 210 for supplying or breaking a power to the heater 100 in accordance with a user's operation; an operation display 710 for displaying whether or not the heater is normally operating; an alarm device 720 for alarming when the heater is operating in error; a temperature indicator 900 for indicating the heating temperature of the heater 100; and a temperature setting button 220 for adjusting the heating temperature of the heater in accordance with a user's operation. If a left side of the button 220 is pushed, the setting temperature drops and if a right side of the button 220 is pushed, the setting temperature rises.

Figure 2:
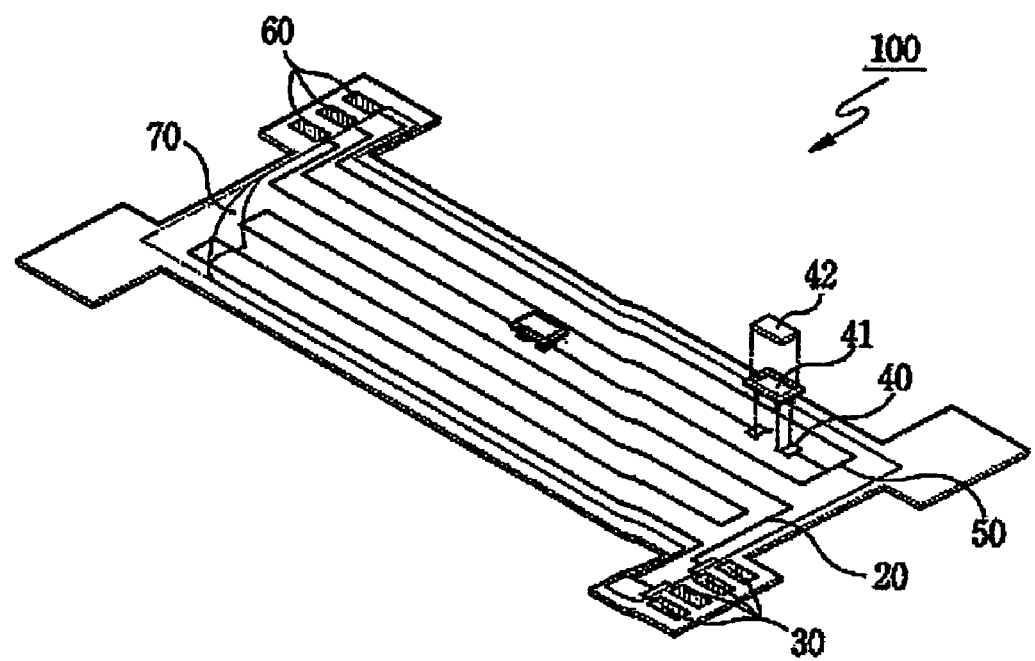
FIG. 2 is a view illustrating an embodiment of heater applied to FIG. 1.

As shown in FIG. 2, the PCB-type heater (100) is formed of an insulating substrate 10; a heating resistor 20 being formed on the upper portion of the insulating substrate by a circuit pattern designed to have a uniform resistance value and generating a heat corresponding to a heat capacity which was re-designed in accordance with the power being supplied; a power supply terminal 30 for supplying a power to the heating resistor 20; a coupling terminal 40 of a temperature sensor mounter 41 mounted thereon with a temperature sensor which measures the temperature of the fluid flowing through the body 110; a sensor connecting terminal 60 being connected to the coupling terminal 40 for reading the measured temperature from the outside; and an insulating protection film 70 for protecting the heating resistor 20.

The sensor mounter 41 is fixedly coupled to the coupling terminal 40, and a sensor 42 is mounted on the sensor mounter 41 and coupled thereto.

Figure 3:
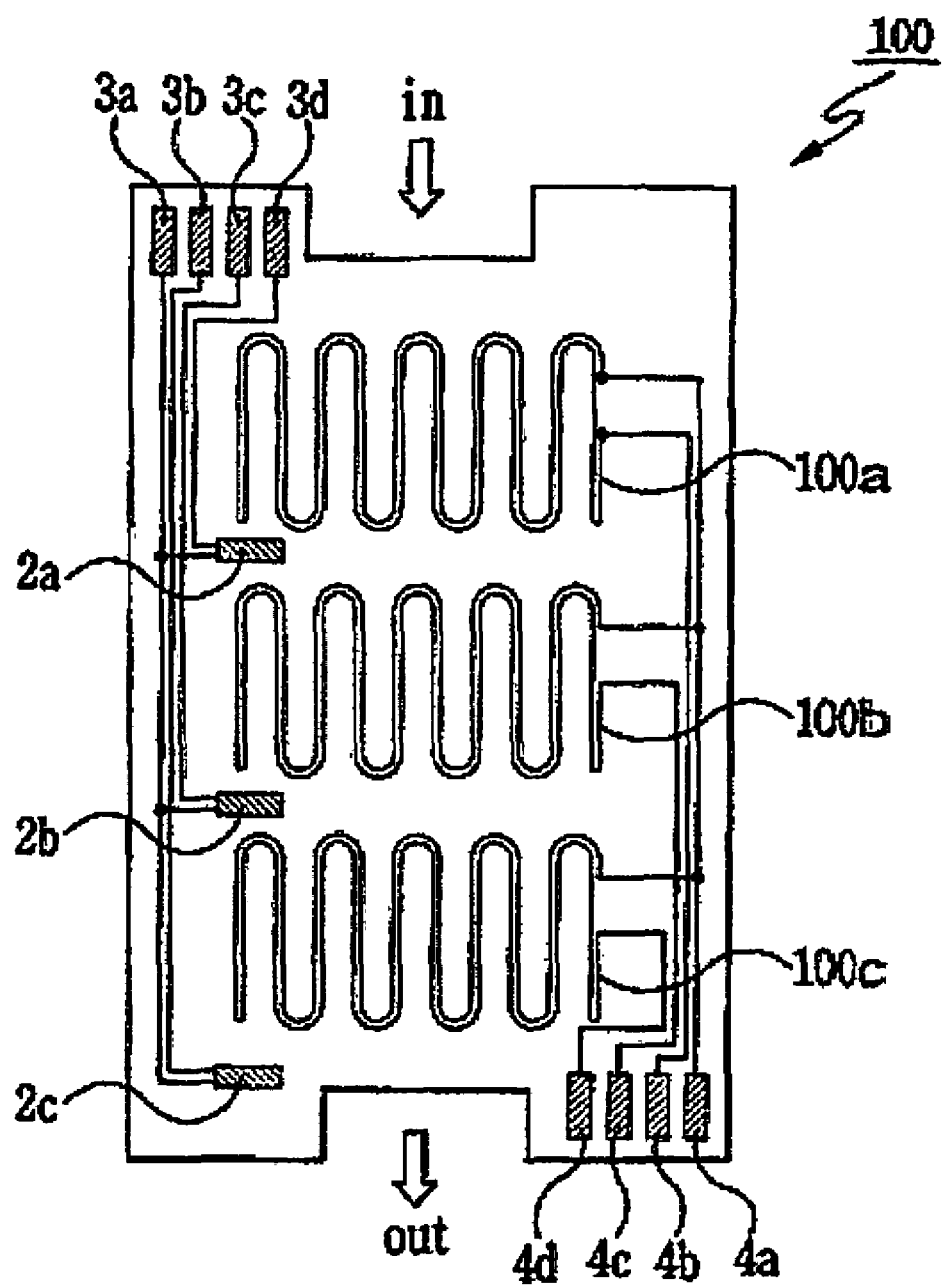
FIG. 3 is a view illustrating other embodiment of heater in FIG. 2.

As shown in FIG. 3, the heater 100 is formed of a plurality of heaters 100a to 100c which are connected in parallel and receive in common a DC power supply. Heating temperature of the heaters 100a to 100c is sensed by sensors 2a to 2c which are connected to the heaters 100a to 100c, respectively. Therefore, when it is required to turn on or off any one of heaters, a control section (not shown in FIG. 3, but shown in FIG. 13) controls switching devices (not shown in FIG. 3) connected to respective heaters 100a to 100c and thus control operations of the heaters by breaking or supplying a DC power to the heaters 100a to 100c. The switching devices may correspond to a safe protection circuit portion in FIG. 13. A reference numeral 3a indicates sensor common line, and reference numerals 3b-3d indicate sensing electrodes being connected to sensors 2a, 2b, respectively. A reference numeral 4a indicates a common line (DC negative electrode) as a power supply terminal, and a reference numerals 4b to 4d indicate DC positive electrodes which are connected to the respective heaters.

Figure 4:
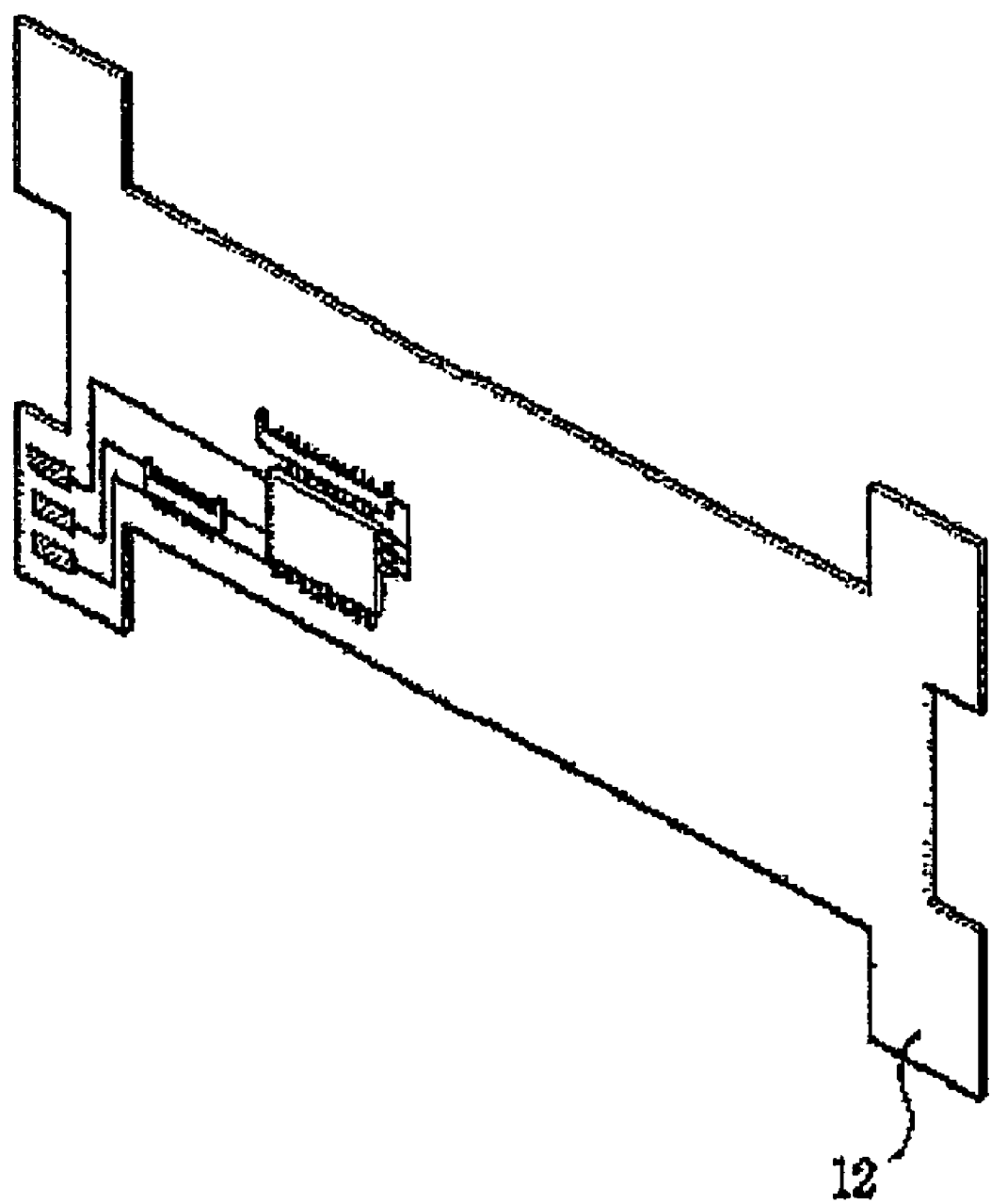
FIG. 4 is a view of a printed circuit board having a control circuit for controlling a heater of FIG. 1 which is mounted on the bottom portion of the board.

Referring to FIG. 4, the heater 100 further comprises a control circuit formed on the bottom portion of the insulating substrate for controlling the degree of heating of the heater.

Now, the function of the control circuit is explained in detail.

Figure 13:
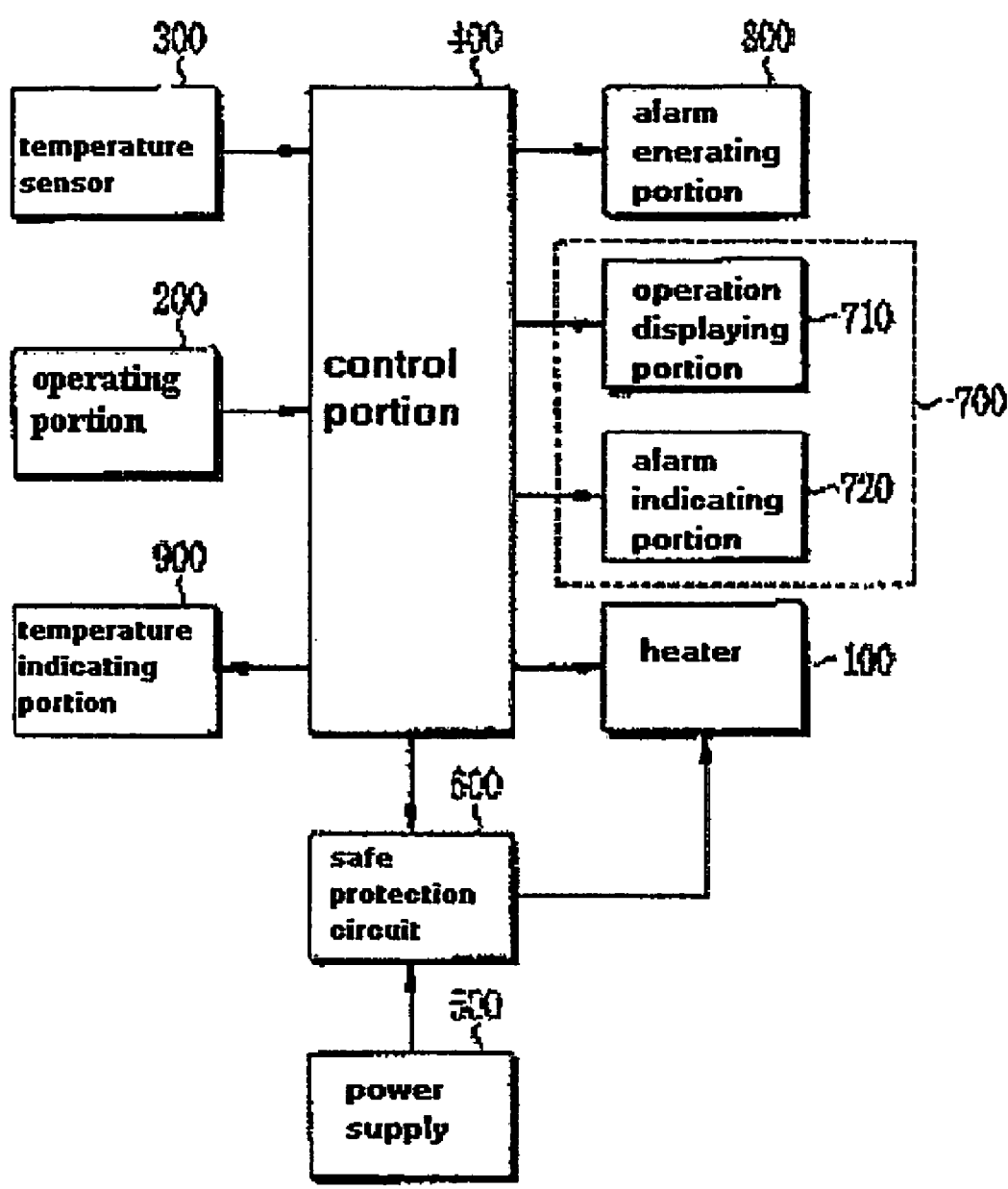
FIG. 13 is a block view illustrating a control circuit for controlling a heating apparatus according to the present invention.

As shown in FIG. 13, the control circuit comprises a power supply portion for supplying a power to the heater 100; a temperature sensor 210 for sensing a heating temperature of the heater 100 and a fluid temperature flowing through the path 112; a power supply button 210 for outputting a power requesting signal in accordance with a user's operation; a operating portion 200 composed of a plurality of buttons such as a temperature setting button 220 for setting the heating temperature; a control portion 400 for allowing a power from the power supply 500 to be supplied to the heater 100 in response to the power requesting signal inputted by the power supply button 210 of the operating portion 200, for controlling the power supplied from the power supply 500 to be interrupted by comparing the setting temperature set by the temperature setting button 220 with the temperature inputted by the temperature sensor 300, lighting the operating display 710 if the power supply button 210 is turned on, and lighting the alarming portion 720 if the heating temperature of the heater 100 is high than a reference temperature; and for controlling the overall system to allow the alarming signal to be transmitted through the alarm generating portion 800; a safe protection circuit portion 600 for supplying or interrupting a power to the heater 100 in response to the control portion 400; and a temperature indicating portion 900 for indicating the set heating temperature of the heater 100 in response to a control signal from the control portion 400.

That is, the control portion 400 controls the power supplied to the heater 100 so that the fluid can maintain a suitable temperature by measuring the heating temperature of the heater 100 as well as the fluid temperature heated by the heater 100 at a uniform temperature.

The operating display 710 is a green-colour light emitting device, the alarming portion is a red-colour light emitting device, which are referred to as light-emitting portion 700 collectively. This configuration may be varied if required. The alarm generating portion 800 may be a buzzer.

Figure 5:
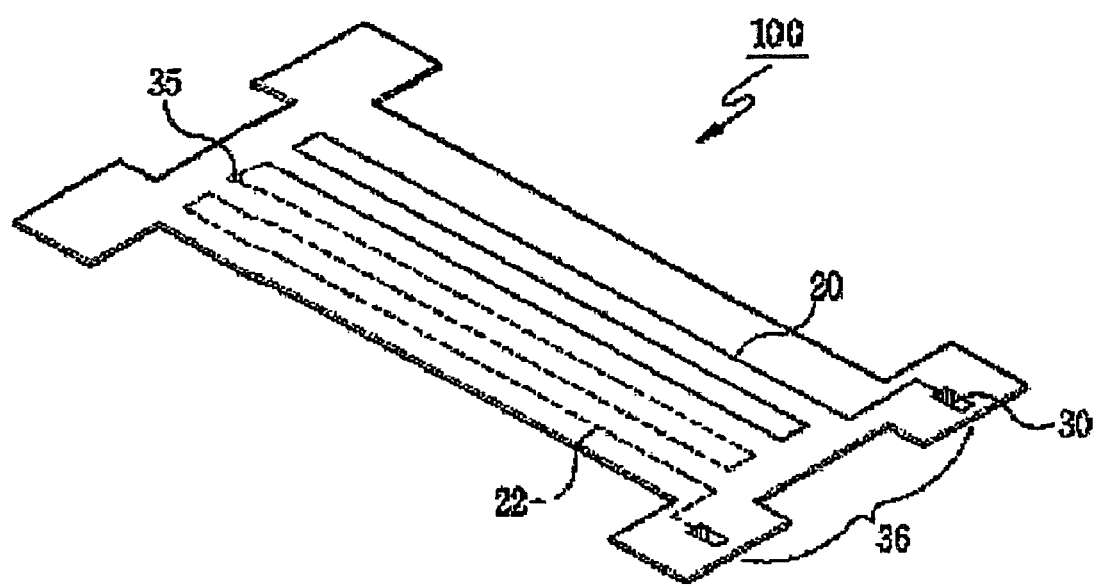
FIG. 5 is a view illustrating other embodiment of FIG. 2.

Instead of the temperature sensor 42 and heater in FIG. 2, as shown in FIG. 5, heating resistors 20, 22 may be formed by coating the one side of the insulating substrate 10 with different materials having large thermoelectric power in order to heat or form a thermocouple in accordance with the power being supplied by allowing the heating resistors to act as a heater if the power is supplied thereto and to act a temperature sensor using the formed thermocouple if power is interrupted. The heating resistor 20, 22 made of two materials is coupled each other by a via hole 35. The components for supplying or interrupting the power to the heating resistors 20, 22 are the safe protection circuit portion 600 and the control circuit portion 400 in FIG. 13.

Figure 6:
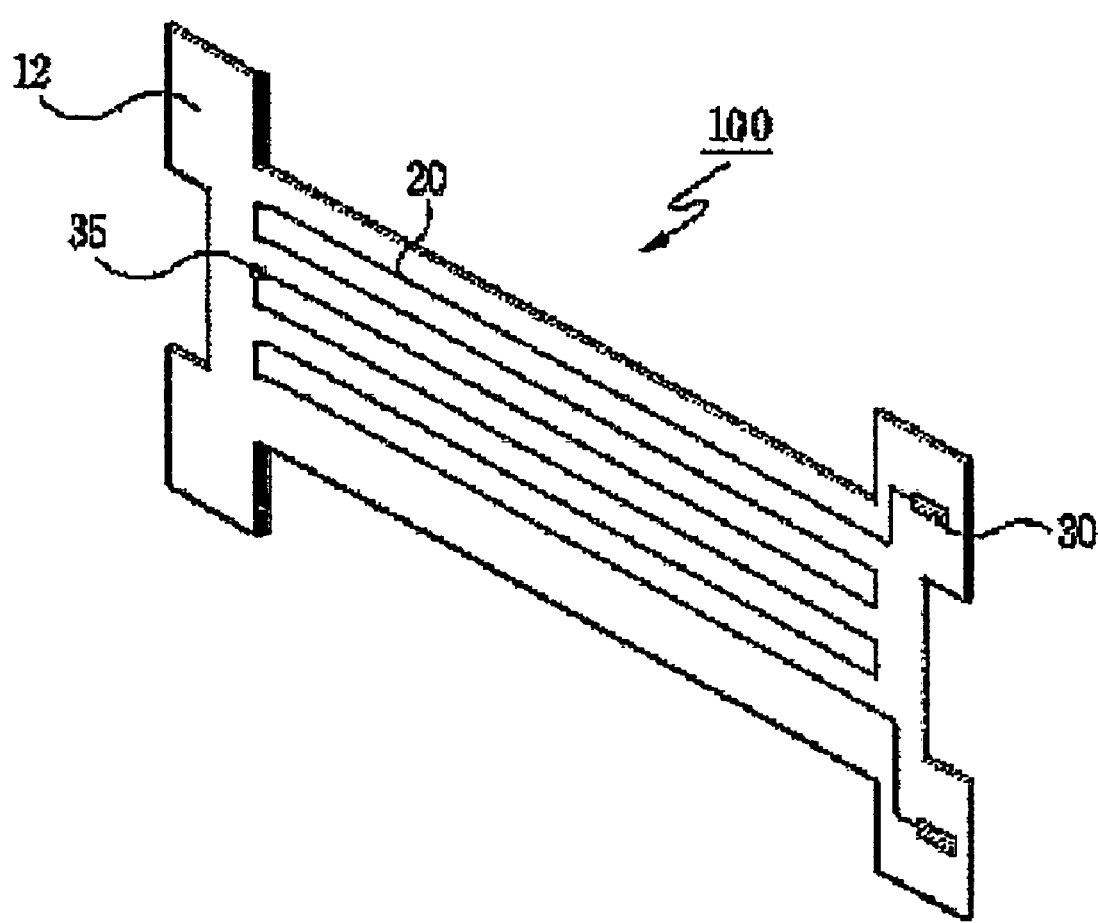
FIGS. 6 and 7 illustrate a upper portion and a bottom portion of another embodiment of FIG. 3, respectively.
Figure 7:
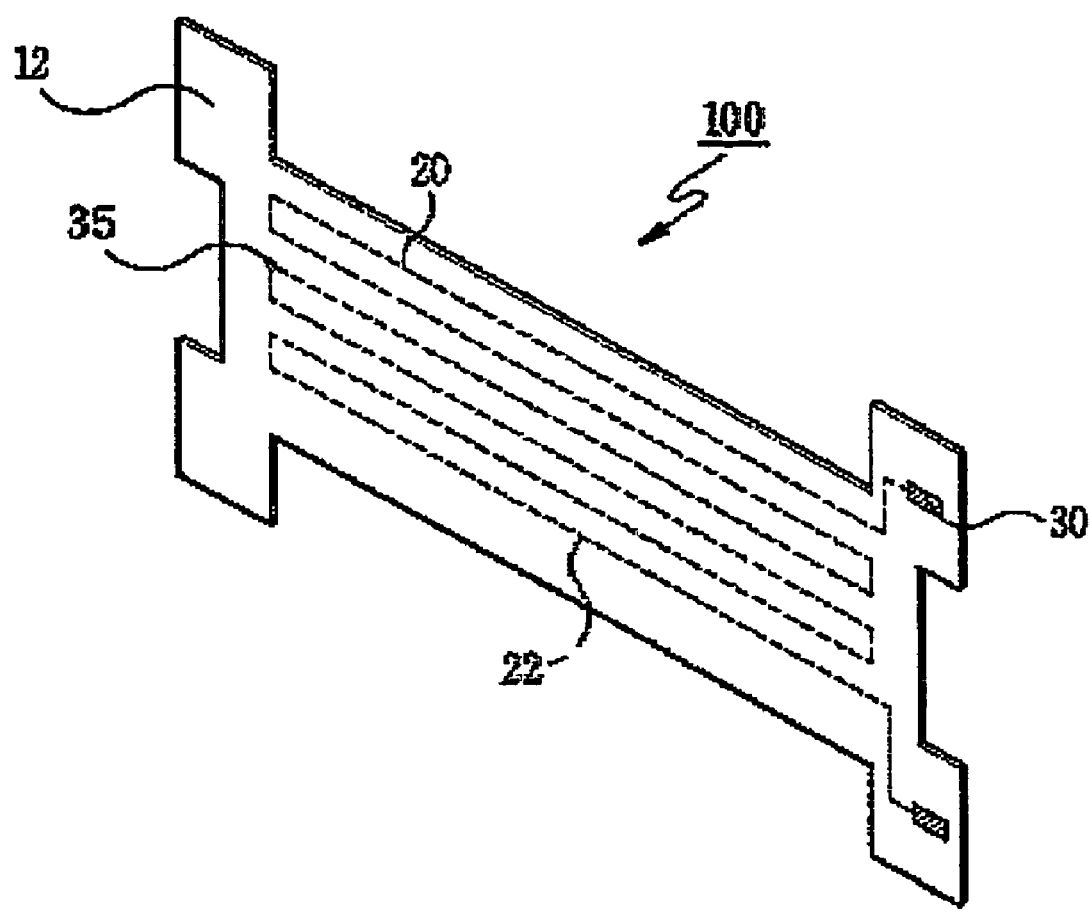

Instead of FIG. 5, as shown in FIGS. 6 and 7, heating resistor 20, 22 are formed by coating the respective upper portion 11 and bottom portion 12 of the insulating substrate with different materials having a large thermoelectric power in order to heat or form a thermocouple in accordance with the power being supplied by allowing the heating resistors to act as a heater if the power is supplied thereto and to act a temperature sensor using the formed thermocouple if power is interrupted. The heating resistor 20, 22 made of two materials are coupled each other by a via hole 35.

Example 2

Figure 8:
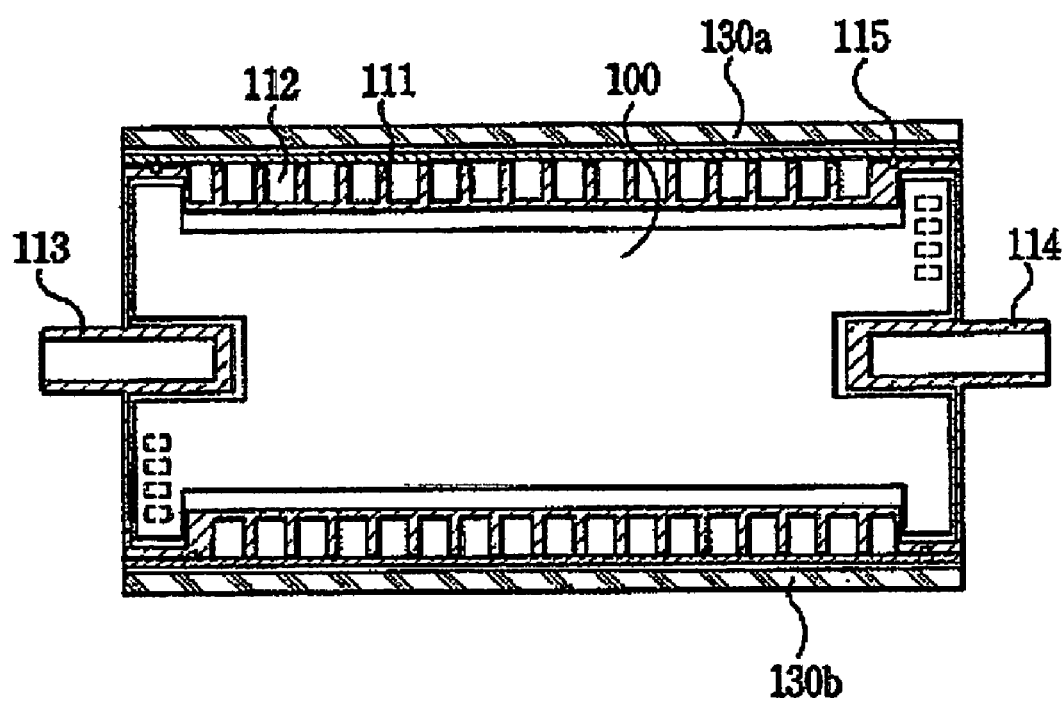
FIG. 8 is a sectional view illustrating other embodiment of FIG. 1.

FIG. 8 is a cross-sectional view of another embodiment of the heating apparatus shown in FIG. 1.

Referring to FIG. 8, the heating apparatus includes a body 110, which includes a first connecting portion 113 having a tube which receives a fluid supplied from an instillation room, a path 112 having the shape of a spiral screw thread to enable the fluid to flow and a second connecting portion for supplying the fluid flowing through the path to an injection syringe, an inner cover 115 inserted into the body 110 and fixedly attached thereto in an ultrasonic mode or a high frequency mode or using adhesive for preventing the fluid from flowing out, middle covers 130a, 130b for closely fixing the body 110 and the inner cover 115 against each other, and a PCB-type heater 100 inserted into the inside of the body 110, for heating the fluid flowing through the path 112 so that the fluid is maintained at a prescribed temperature.

Though not shown in the drawing, in the same manner as the first embodiment, the heating apparatus further include a bottom case 150 having a box portion 151 to receive the body 110 having the heater 100 and the middle covers 130a, 130b coupled thereto, and a upper case 140 coupled to the bottom case 150.

The second embodiment is the same as the first embodiment except for a location into which the heater 110 is inserted. Thus, description on them will be omitted for simplicity.

Example 3

Figure 9:
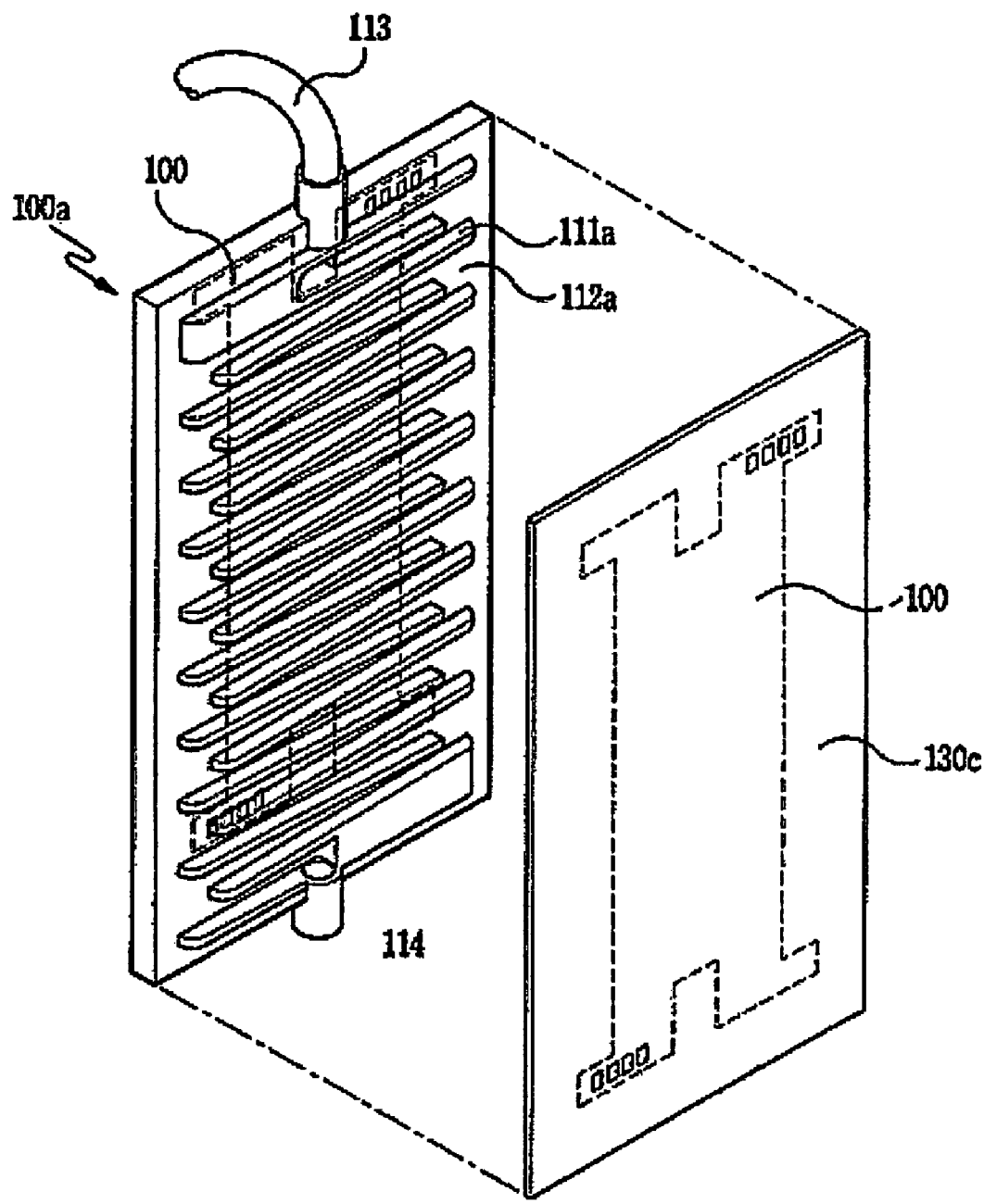
FIG. 9 is a sectional view another embodiment of FIG. 1.

FIG. 9 is a cross-sectional view of another embodiment of the heating apparatus shown in FIG. 1.

Referring to FIG. 9, the heating apparatus includes a body 110a, which includes a first connecting portion 113 having a tube which is connected to the first connection portion and receives a fluid supplied from an instillation room, a path 112a having the shape of a zigzag to enable the fluid to flow, and a second connecting portion 114 for supplying the fluid flowing through the path 112a to an injection syringe, a middle cover 130c adhered to a surface where the path 112a is formed in an ultrasonic, a high frequency or adhesive manner, for preventing the fluid from flowing out, and a PCB-type heater 100 inserted into at least one inside of the inside of the body 112a and the inside of the middle cover 130c for heating the fluid flowing through the path 112a so that the fluid is maintained at a prescribed temperature.

In this time, the path 112a is formed by a projection 111a.

Though not shown in the drawing, in the same manner as the first embodiment, the heating apparatus further include a bottom case 150 having a box portion 151 to receive the body 110 having the heater 100 and the middle cover 130c coupled thereto, and a upper case 140 coupled to the bottom case 150.

The path 112a has the shape of the zigzag in the third embodiment, but has the shape of the spiral screw thread in the first embodiment. Furthermore, the third embodiment is the same as the first embodiment except for a location into which the heater 110 is inserted. Thus, description on them will be omitted for simplicity.

Figure 10:
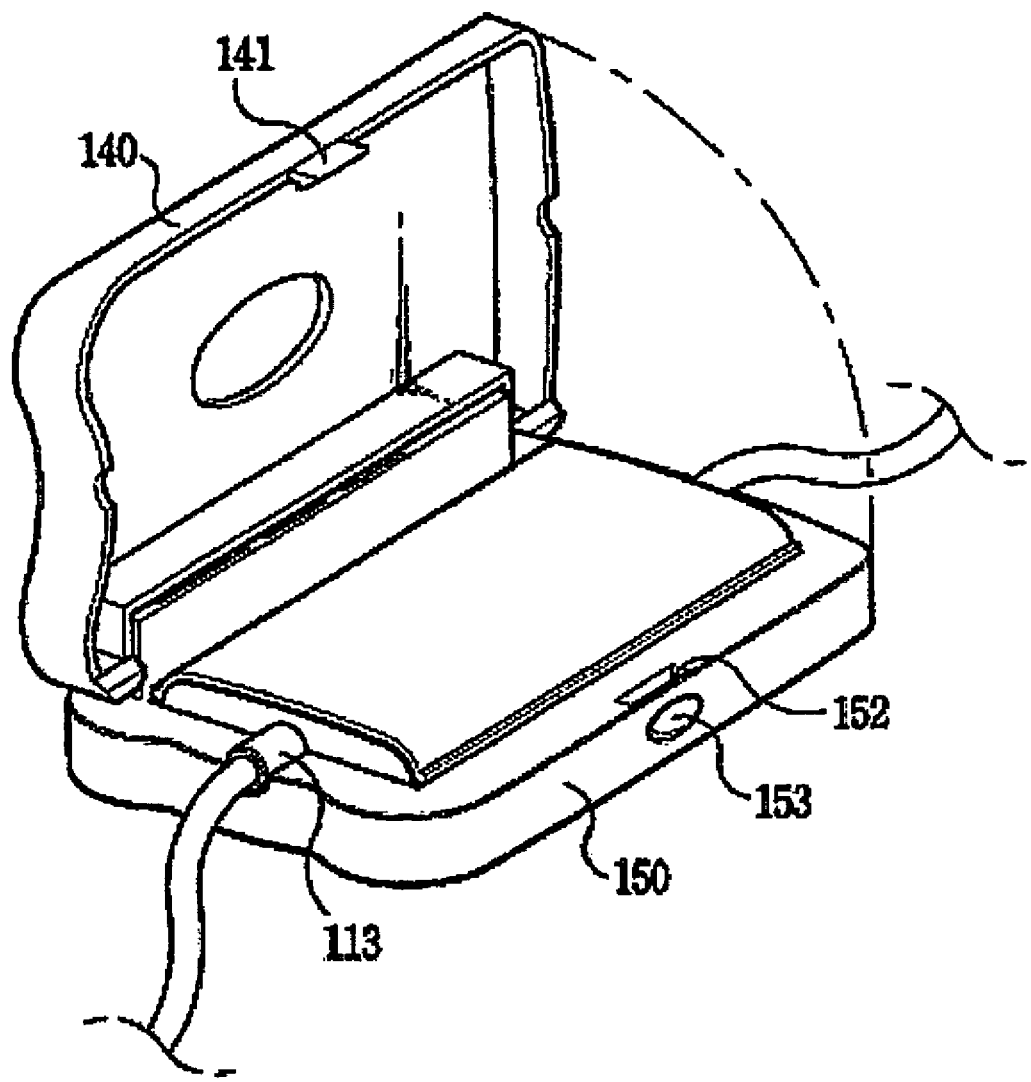
FIG. 10 is a combined prospective view of FIG. 1.

FIG. 10 is a perspective view showing the heating apparatus is coupled in FIG. 1.

Referring to FIG. 10, a protrusion for locking 141 having a projection for fixing formed in is formed in the upper cover 140. A groove 152 to which the protrusion 141 is coupled is formed in the bottom cover 150. A button 153, which enables the protrusion 141 coupled to the groove 152 to be deviated from the groove 152 when a user depresses the groove 152, is formed in the groove 152.

Figure 11:
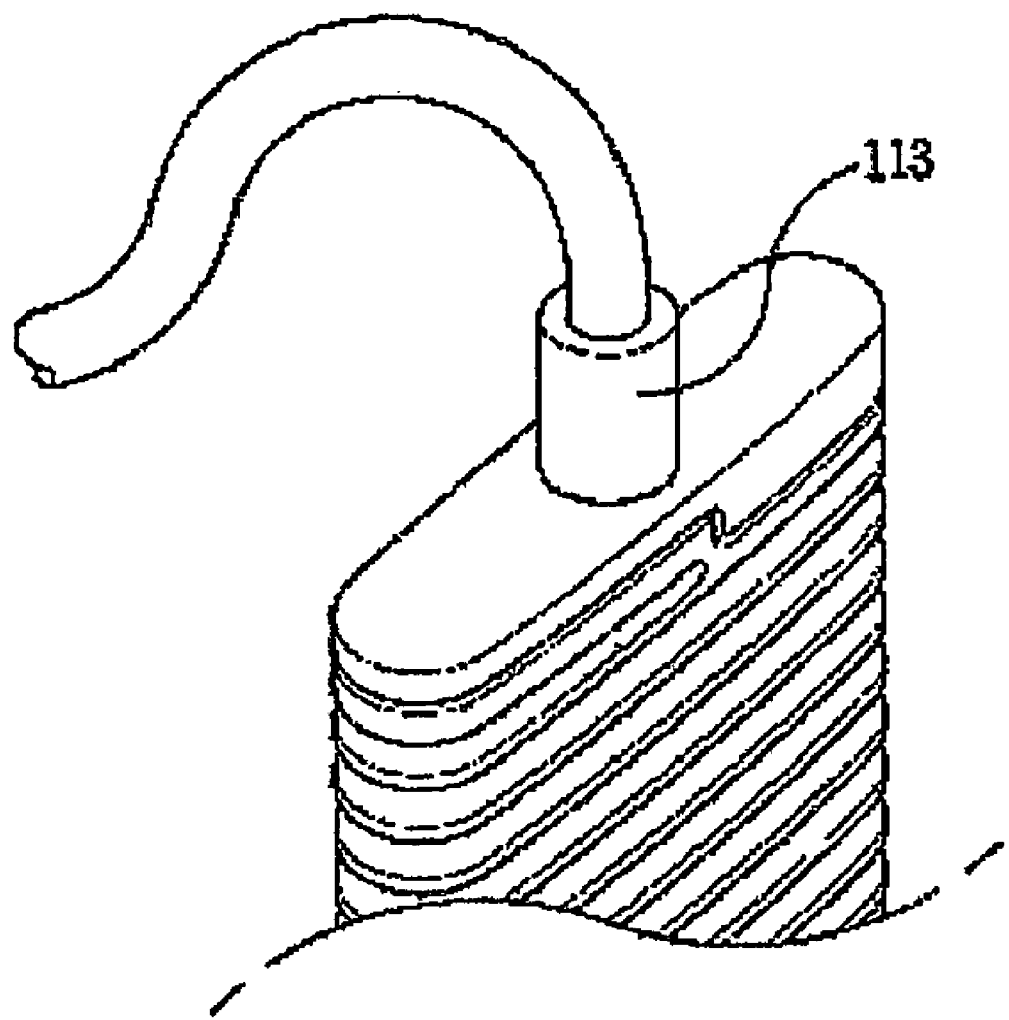
FIG. 11 is a view illustrating an instillation room connecting portion to which the present invention is applied.

FIG. 11 shows a connection portion of the instillation room to which the present invention is applied. FIG. 11 shows a method in which the tube for enabling Ringer's solution or blood to be introduced from the instillation room to the path 112 of the body 110 is coupled to the connection portion 113. In this method, after the end of the tube is inserted into the connection portion 113, the tube is closely inserted into and fixed to the connection portion 113 by means of a downward force. In this time, the body 110 and the tube are made of the same material, PVC, and are thus fixed and coupled using an adhesive.

Figure 12:
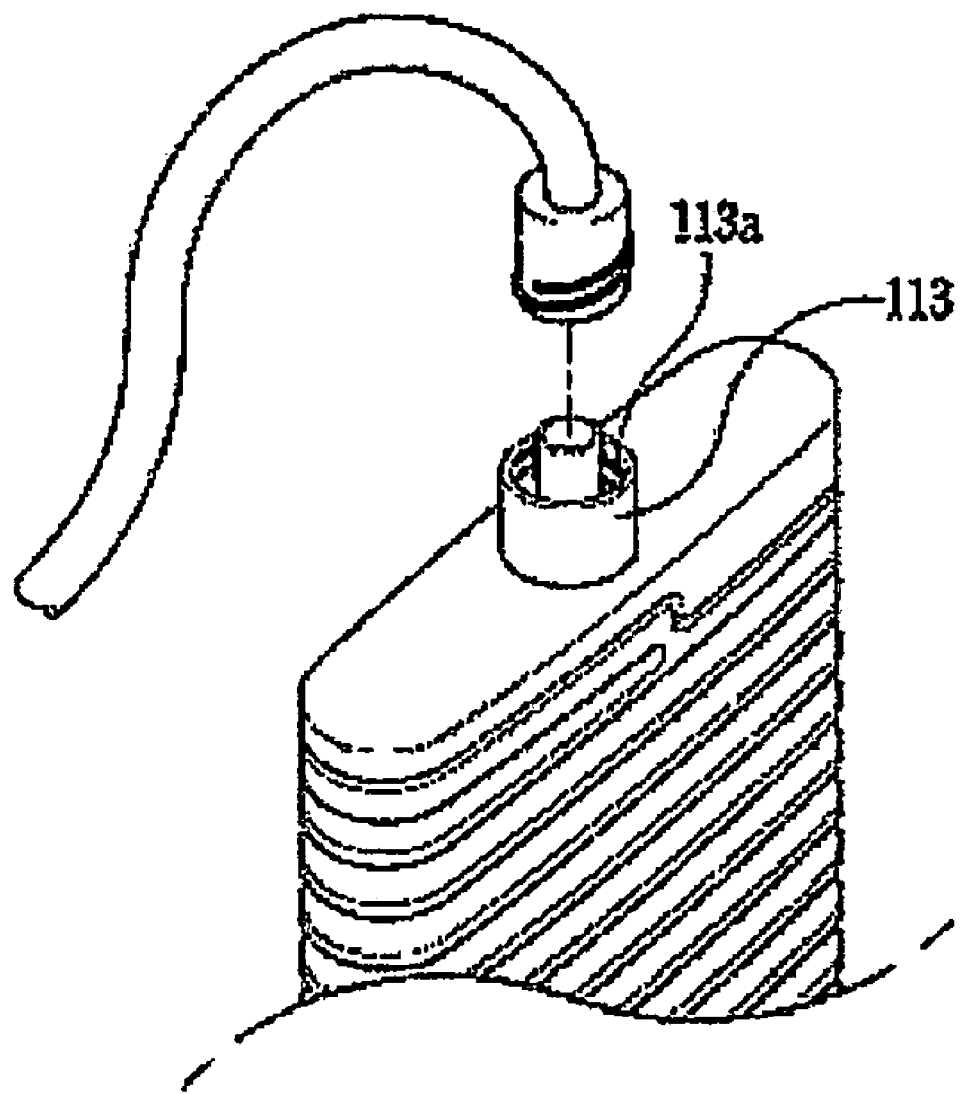
FIG. 12 is a view illustrating other embodiment of FIG. 11.

FIG. 12 a cross-sectional view of another embodiment of the heating apparatus shown in FIG. 1. In FIG. 11, a female screw crest 113a is formed within the connection portion 113 of FIG. 9 and a coupling member is formed to the end of the tube.

A male screw crest is formed on the outside of the coupling member formed at the end of the tube. The male screw crest coupled to the female screw crest 113a serves to maintain the fluid supplied through the tube at a given temperature by means of a heating machine. In this time, the material of the tube is PVC in the same manner as FIG. 12, but the material of the body 110 is PP unlike FIG. 12. Thus, the tube and the body cannot be coupled using an adhesive because the materials thereof are different. The heating apparatus shown in FIG. 12 has a screw coupling structure.

Example 4

Figure 14:
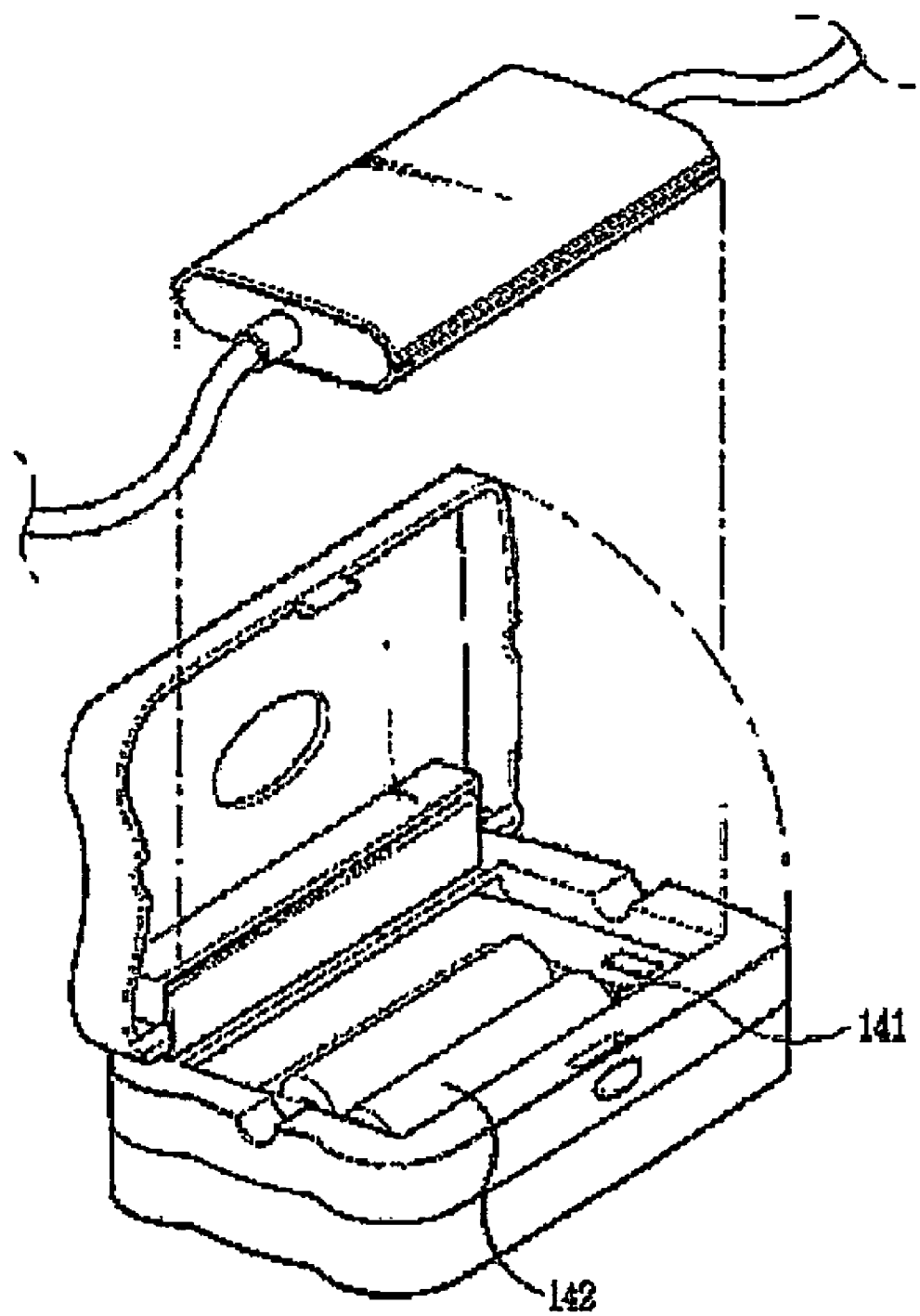
FIG. 14 is a exposed view of a DC power supply as still another embodiment of FIG. 1.

As shown in FIGS. 1 and 14, the heating apparatus includes a body 110, which includes a first connecting portion 113 having a tube which is connected to the first connection portion and receives a fluid supplied from an instillation room, a path 112 having the shape of a spiral screw thread to enable the fluid to flow, and a second connecting portion 114 for supplying the fluid flowing through the path 112 to an injection syringe, an inner cover 115 inserted into the body 110 and fixedly attached thereto in an ultrasonic, high frequency or adhesive manner for preventing the fluid from flowing out, middle covers 130a, 130b for closely fixing the body 110 and the inner cover 115 against each other, and a PCB-type heater 100 inserted into at least one inside of the upper surface 130a and the bottom surface 130b of the middle cover 130c and the inside of the body 110 for heating the fluid flowing through the path 112 so that the fluid is maintained at a prescribed temperature, a bottom case 150 having a box portion 151 to receive the body 110 having the heater 100 and the middle covers 130a, 130b coupled thereto, a upper case 140 coupled to the bottom case 150 and having power supply terminals 140 to supply a power to the heater, and a DC power supply unit 142 mounted on the inside of the upper case to allow the battery to contact with the power supply terminals 141.

The remaining construction of this embodiment is the same as those of the first embodiment. Thus, description on them will be omitted for simplicity. That is, the fourth embodiment is designed to receive the power for driving the heater through a batter being a DC power. In this time, the DC power supply unit 142 may include a DC adaptor for supplying a constant voltage, in addition to the battery shown in the drawing.

Example 5

Figure 15:
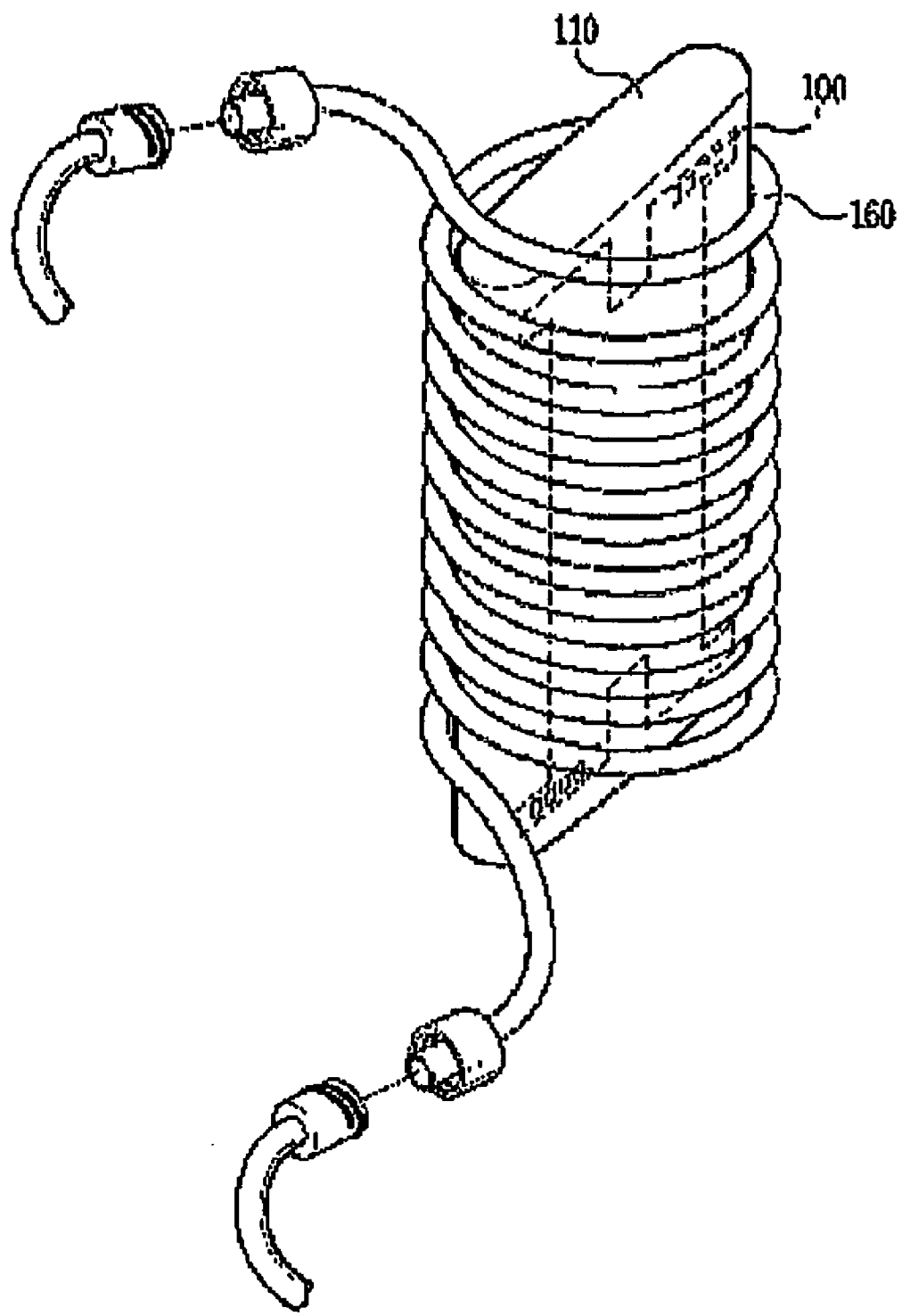
FIG. 15 is a view illustrating further still another embodiment of FIG. 1.

Referring to FIG. 15, a heating apparatus includes a body 110 having a PCB-type heater 100 inserted thereinto, a tube 160 wound around the upper portion of the body 110 for moving a prescribed fluid and maintaining the fluid at an uniform temperature, and rigid middle covers 130a, 130b coupled to the body 100 to allow the tube 160 to be fixedly attached to the body 110.

The remaining construction of this embodiment is the same as those of the first embodiment. Thus, description on them will be omitted for simplicity.

Hereinafter, the operation of the heating apparatus having the PCB-type heater will be described.

According to the connection method shown in FIG. 1 or 12, if the tube connected to the instillation room is coupled to the first connection portion 113 of the heating apparatus, the tube connected to the injection syringe is coupled to the second connection portion 114, a user turns on the power supply button 210 and a temperature is set by a temperatures setting button 220, a control circuit 400 shown in FIG. 13 controls a safety protection circuit 600 to supply the power of the power supply unit 500 to the heater 100. In this time, the control circuit 400 controls an operational display 710 to be lighted. Therefore, the user can know that the heating apparatus operates normally through the operational display 710.

Furthermore, the control circuit 400 continues to check a heating temperature of the heater 100 through the temperature sensor 300. It determines whether the temperature checked by the temperature sensor 300 is coincident with the temperature set by the user. If it is determined that the temperature checked by the temperature sensor 300 is coincident with or less than the temperature set by the user, the control circuit 400 controls the safety protection circuit 600 to supply the power to the heater 100 and then checks the heating temperature of the heater 100 through the temperature sensor 300. Meanwhile, if it is determined that the temperature checked by the temperature sensor 300 is higher than the temperature set by the user, the control circuit 400 controls the safety protection circuit 600 to shut the power supplied to the heater 100.

Meanwhile, if it is determined that the temperature of the heater 100 sensed through the temperature sensor 300 is higher than the heating temperature set as a reference, the control circuit 400 controls an alarm display unit 720 to be lighted, while controlling the safety protection circuit 600 to shut the power supplied to the heater 100. Also, the control circuit 400 controls an alarm device 800 to generate an alarm signal. Thus, the user can know that the heating apparatus operates erroneously from the alarm signal.

INDUSTRIAL APPLICABILITY

According to the present invention, by using a PCB-type heater having a accurate resistance values, the heating apparatus can allow the temperature of Ringer's solution or blood which is introduced into a blood vessel, when transfusing a blood thereto, to be equal to that of the human body, prevent any temperature declination and cold pain of the human's body caused when there is a difference between them.

Also, since the present invention can accurately design a resistance value of heater, a heating temperature which should be set by heating apparatus for medicine can be correctly provided.

Further, by forming a heating resister on a printed circuit board using two different materials having a large thermoelectric power and forming a thermocouple by the two materials, the heating temperature of the heating can be measured and controlled.

Further, it is possible to provide an efficient and low-priced heating apparatus for medicine having an accurate temperature by forming a heater in a printed circuit board type.

Finally, by utilizing the power supply of the heater as DC power supply, it is convenient to use and can be used conveniently under the situation that commercial power supply can not be provided.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

The invention claimed is:

1. A heating apparatus, comprising:
a body comprising a first connecting portion to receive an unheated fluid from an external source, a second connecting portion to supply a heated fluid and a path for said unheated fluid to flow in from the first connecting portion and out from the second connecting portion; and
a printed circuit board type (PCB-type) heater formed on an insulating substrate comprises a heating resistor formed on both surfaces of said insulating substrate and resides inside of the body; and
wherein said path wraps around said PCB-type heater multiple times to heat said unheated fluid flowing through said path from the first connecting portion to supply said heated fluid at the second connecting portion.

2. The heating apparatus of claim 1, wherein said path has a shape of a spiral screw thread or a zigzag.

3. The heating apparatus of claim 1, wherein said PCB-type heater further comprises one or more additional heating resistors form on said insulating substrate to additionally heat said unheated fluid flowing through said path.

4. The heating apparatus of claim 1, wherein said heating resistor is formed by coating said insulating substrate with different materials having a large thermoelectric power.

5. The heating apparatus of claim 4, wherein said insulating substrate is coated with one or more of the following: copper, iron, chrome and an alloy composed of the combination of the materials at a prescribed rate.

6. The heating apparatus of claim 1, wherein said insulating substrate further comprises a power supply terminal to receive power from an external power source and supply power from the external power source to said heating resistor of said PCB-type heater; and wherein said PCB-type heater further comprises a control circuit to control power supplied to said heating resistor from said power supply terminal.

7. The heating apparatus of claim 6, wherein said PCB-type heater further comprises a temperature sensor for measuring temperature of said heating resistor; and wherein said control circuit cuts power to said heating resistor if said temperature sensor determines that the heating temperature of the heating resistor exceeds a reference temperature.

8. The heating apparatus of claim 6, wherein said PCB-type heater further comprises a temperature sensor for measuring temperature of said heating resistor; wherein said insulating substrate further comprises a sensor connecting terminal connected to said temperature sensor; and wherein the heating apparatus is installable in a housing adapted to house the heating apparatus and connect to said power terminal and said sensor connecting terminal of the heating apparatus.

9. The heating apparatus of claim 8 is installable in said housing comprising at least one of the following:
a temperature setting button to adjust a heating temperature of said PCB-type heater by an operator; and wherein said control circuit controls power supplied to said heating resistor to maintain said PCB-type heater at said heating temperature;
an alarm indicator to display or output an alarm signal generated by said control circuit when said temperature sensor determines that a heating temperature of the heating resistor exceeds a reference temperature;
a temperature indicator connected to said sensor connecting terminal to display the temperature of said PCB-type heater as measured by said temperature sensor; and
an adapter connected to said power terminal to supply power from the external power source to said heating resistor.

10. The heating apparatus of claim 1, wherein each of said first and second connecting portions has a coupling member to receive a tube supplying said unheated fluid to said body or receiving said heated fluid from said body.

11. A heating apparatus, comprising:
a printed circuit board type (PCB-type) heater formed on an insulating substrate comprises a heating resistor formed on both surfaces of said insulating substrate; and
a path formed on said both surfaces of said insulating substrate wraps around said PCB-type heater multiple times to heat an unheated fluid flowing through said path from a first end of said path receiving said unheated fluid from an external source to a second end of said path providing a heated fluid, said path forming a body surrounding said PCB-type heater.

12. The heating apparatus of claim 11, wherein said path has a shape of a spiral screw thread or a zigzag.

13. The heating apparatus of claim 11, wherein said PCB-type heater further comprises one or more additional heating resistors form on said insulating substrate to additionally heat said unheated fluid flowing through said path.

14. The heating apparatus of claim 11, wherein said heating resistor is formed by coating said insulating substrate with different materials having a large thermoelectric power.

15. The heating apparatus of claim 14, wherein said insulating substrate is coated with one or more of the following: copper, iron, chrome and an alloy composed of the combination of the materials at a prescribed rate.

16. The heating apparatus of claim 11, wherein said insulating substrate further comprises a power supply terminal to receive power from an external power source and supply power from the external power source to said heating resistor of said PCB-type heater; and wherein said PCB-type heater further comprises a control circuit to control power supplied to said heating resistor from said power supply terminal.

17. The heating apparatus of claim 16, wherein said PCB-type heater further comprises a temperature sensor for measuring temperature of said heating resistor; and wherein said control circuit cuts power to said heating resistor if said temperature sensor determines that the heating temperature of the heating resistor exceeds a reference temperature.

18. The heating apparatus of claim 16, wherein said PCB-type heater further comprises a temperature sensor for measuring temperature of said heating resistor; wherein said insulating substrate further comprises a sensor connecting terminal connected to said temperature sensor; and wherein the heating apparatus is installable in a housing adapted to house the heating apparatus and connect to said power terminal and said sensor connecting terminal of the heating apparatus.

19. The heating apparatus of claim 18 is installable in said housing comprising at least one of the following:

a temperature setting button to adjust a heating temperature of said PCB-type heater by an operator; and wherein said control circuit controls power supplied to said heating resistor to maintain said PCB-type heater at said heating temperature;

an alarm indicator to display or output an alarm signal generated by said control circuit when said temperature sensor determines that a heating temperature of the heating resistor exceeds a reference temperature;

a temperature indicator connected to said sensor connecting terminal to display the temperature of said PCB-type heater as measured by said temperature sensor; and an adapter connected to said power terminal to supply power from the external power source to said heating resistor.

20. The heating apparatus of claim 11, wherein each of said first and second connecting portions has a coupling member to receive a tube supplying said unheated fluid to said body or receiving said heated fluid from said body.

* * * * *